US008486695B2

(12) United States Patent
Danilkovitch et al.

(10) Patent No.: US 8,486,695 B2
(45) Date of Patent: Jul. 16, 2013

(54) MESENCHYMAL STEM CELLS EXPRESSING TNF-ALPHA RECEPTORS

(75) Inventors: Alla Danilkovitch, Columbia, MD (US); Diane Carter, Huntington, MD (US); Alicia Tyrell, Catonsville, MD (US); Simon Bubnic, Ann Arbor, MI (US); Michelle Marcelino, Ijamville, MD (US); Rodney Monroy, Aberdeen, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 13/402,498

(22) Filed: Feb. 22, 2012

(65) Prior Publication Data

US 2012/0214178 A1    Aug. 23, 2012

Related U.S. Application Data

(63) Continuation of application No. 12/091,391, filed as application No. PCT/US2007/000274 on Jan. 5, 2007, now abandoned.

(60) Provisional application No. 60/759,157, filed on Jan. 13, 2006.

(51) Int. Cl.
*C12N 5/08* (2006.01)
*G01N 33/53* (2006.01)
*A01N 63/00* (2006.01)

(52) U.S. Cl.
USPC ............................................ 435/372; 435/7.1

(58) Field of Classification Search
USPC .................................................. 435/372, 7.1
See application file for complete search history.

(56) References Cited

U.S. PATENT DOCUMENTS

| 5,486,359 | A | 1/1996 | Caplan et al. |
| 6,007,995 | A | 12/1999 | Baker et al. |
| 6,071,889 | A | 6/2000 | Weiss et al. |
| 6,797,514 | B2 | 9/2004 | Berenson et al. |
| 7,037,492 | B2 * | 5/2006 | Glorioso et al. ............ 424/93.2 |
| 2004/0033214 | A1 | 2/2004 | Young et al. |
| 2004/0241141 | A1 | 12/2004 | Pawliuk et al. |
| 2006/0063141 | A1 | 3/2006 | McGann et al. |
| 2007/0258963 | A1 | 11/2007 | Danilkovitch et al. |

FOREIGN PATENT DOCUMENTS

WO        2005093044 A1    10/2005

OTHER PUBLICATIONS

Bilic, G. et al., "In vitro lesion repair by human amnion epithelial and mesenchymal cells", Amer. Journal of Obstetrics and Gynecology, vol. 190, No. 1, Jan. 2004, pp. 87-92, XP009164009.
Tarte, K. et al., INF-Gamma, Unlike TNF-Alpha, LPS, or CD40 Signal, is Required and Sufficient to Induce Indoleamine 2,3- Dioxygenase Activity in Mesenchymal Stem Cells, Blood, Amer. Society of Hematology, US, vol. 106, No. 11, (2005), p. 650A, XP008080026.
Barbet, R., et al., Stem Cells Int. 2011:1-9, 2011, Article ID 368192.
Wu et al., Transplantation, 75:679-685 (2003).
Wu et al., J. Neurosci. Res., 72:393-404 (2003).
Aggarwal et al., Blood 105:1815-1822 (2005).
Ballas et al., J. Cell. Biochem. Suppl., 38:20-28 (2002).
Chopp et al., Neuroreport, 11:3001-3005 (2000).
Czitrom, Clin. Orthop. Relat. Res., 326:11-24 (1996).
Deans et al., Exp. Hematol., 28:875-884 (2000).
Debets et al., Cytokine, 8:80-88 (1996).
DeKok et al., Clin. Oral Implants Res., 14:481-489 (2003).
Di Nicola et al., Blood, 99:3638-3843 (2002).
Eaves et al., Ann. NY Acad. Sci., 938:63-70 (2001).
Ellison et al., J. Clin. Immunol., 24:197-211 (2004).
Foster et al., Transplantation, 76(6):988-994 (2003).
Frassoni et al., Int. Society for Cell Therapy, SA 006 (abstract) (2002).
Fukuda, Artif. Organs, 25:187-193 (2001).
Gerstenfeld et al., Cells Tissues Organs, 169:285-294 (2001).
Haynesworth et al., Bone, 13:69-80 (1992).
Horwitz et al., Blood, 97:1227-1231 (2001).
Horwitz et al., Proc. Natl. Acad. Sci. USA, 99:8932-8937 (2002).
Koc et al., J. Clin. Oncol., 18:307-316 (2000).
Koide et al., Transplantation, 64:518-524 (1997).
Koulova et al., J. Exp. Med., 173(3):759-762 (1991).
Kuroiwa et al., J. Clin. Invest., 107:1365-1373 (2001).
Le Blanc et al., The Lancet., 363:1439-1441 (2004).
Mackenzie et al., Blood Cells Mol. Dis., 27:601-604 (2001).
Noel et al., Curr. Opin. Investig. Drugs, 3:1000-1004 (2002).
Ojwang et al., Biochemistry, 36:6033-6045 (1997).
Pereira et al., Proc. Natl. Acad. Sci. USA, 95:1142-1147 (1998).
Pittenger et al., Science, 284:143-147 (1999).
Prockop, Science, 276:71-74 (1997).
Sanchez-Ramos et al., Exp. Neurol., 171:109-115 (2001).
Schwartz et al., Hum. Gene Ther., 10:2539-2549 (1999).
Shake et al., Ann. Thorac. Surg., 73:1919-1925 (2002).
Shen et al., J. Biol. Chem., 272:3550-3553 (1997).
Tartaglia et al., Proc. Natl. Acad. Sci. USA, 88:9292-9296 (1991).
Toma et al., Circulation, 105:93-98 (2002).
Tomita et al., Circulation, 100(suppl II):II-247-II-256 (1999).
Trickett et al., J. Immunol. Methods, 275:251-255 (2003).
Tse et al., Transplantation, 75:389-397 (2003).
Vancheri et al., Am. J. Respir. Cell Mol. Biol., 22:628-634 (2000).
Wagers et al., Gene Ther., 9:606-612 (2002).
Wakitani et al., Muscle Nerve, 18:1417-1426 (1995).
Woodbury et al., J. Neurosci. Res., 69:908-917 (2002).

* cited by examiner

*Primary Examiner* — Quang Nguyen
(74) *Attorney, Agent, or Firm* — McAndrews, Held & Malloy, Ltd.

(57) ABSTRACT

Mesenchymal stem cells which express TNF-α receptor Type I in an amount of at least 13 pg/$10^6$ cells. Such mesenchymal stem cells inhibit the proliferation of lymphocytes and may be employed, in particular, in the treatment of graft-versus-host disease.

5 Claims, 2 Drawing Sheets

MESENCHYMAL STEM CELLS EXPRESSING TNF-ALPHA RECEPTORS

This application is a continuation of U.S. patent application Ser. No. 12/091,391 filed Sep. 15, 2008, now abandoned which is a National Stage Entry of international patent application number PCT/US07/00274, filed on Jan. 5, 2007, which claims priority to U.S. Provisional Patent Application Ser. No. 60/759,157, filed on Jan. 13, 2006.

This application claims priority based on application Ser. No. 60/759,157, filed Jan. 13, 2006, the contents of which are incorporated by reference in their entirety.

This invention relates to mesenchymal stem cells. More particularly, this invention relates to mesenchymal stem cells which express tumor necrosis factor-alpha (TNF-α) receptors, and in particular, the tumor necrosis factor-alpha (TNF-α) receptor Type I (TNFRI), in an amount of at least 13 pg/$10^6$ cells. Such mesenchymal stem cells inhibit lymphocyte proliferation.

Mesenchymal stem cells (MSCs) are multipotent stem cells that can differentiate readily into lineages including osteoblasts, myocytes, chondrocytes, and adipocytes (Pittenger, et al., *Science*, 284, pg. 143 (1999); Haynesworth, et al., *Bone*, Vol. 13, pg. 69 (1992); Prockop, *Science*, Vol. 276, pg. 71 (1997)). In vitro studies have demonstrated the capability of MSCs to differentiate into muscle (Wakitani, et al., *Muscle Nerve*, Vol. 18, pg. 1417 (1995)), neuronal-like precursors (Woodbury, et al., *J. Neurosci. Res*. Vol. 69, pg. 908 (2002); Sanchez-Ramos, et al., *Exp. Neurol.*, Vol. 171, pg. 109 (2001)), cardiomyocytes (Tome, et al., *Circulation*, Vol. 105, pg. 93 (2002); Fakuda, *Artif. Organs*, Vol. 25, pg. 187 (2001)) and possibly other cell types. In addition, MSCs have been shown to provide effective feeder layers for expansion of hematopoietic stem cells (Eaves, et al., *Ann. N.Y. Acad. Sci.*, Vol. 938, pg. 63 (2001); Wagers, et al., *Gene Therapy*, Vol. 9, pg. 606 (2002)). Recent studies with a variety of animal models have shown that MSCs may be useful in the repair or regeneration of damaged bone, cartilage, menisous or myocardial tissues (DeKok, et al., *Clin. Oral Implants Res.*, Vol. 14, pg. 481 (2003)); Wu, et al. *Transplantation*, Vol. 75, pg. 679 (2003); Noel, et al., *Curr. Opin. Investig. Drugs*, Vol. 3, pg. 1000 (2002); Ballas, et al., *J. Cell. Biochem. Suppl.*, Vol. 38, pg. 20 (2002); Mackenzie, et al., *Blood Cells Mol. Dis.*, Vol. 27, pgs. 601-604 (2001)). Several investigators have used MSCs with encouraging results for transplantation in animal disease models including osteogenesis imperfecta (Pereira, et al., *Proc. Nat. Acad. Sci.*, Vol. 95, pg. 1142 (1998)), parkinsonism (Schwartz, et al., *Hum. Gene Ther.*, Vol. 10, pg. 2539 (1999)), spinal cord injury (Chopp, et al., *Neuroreport*, Vol. 11, pg. 3001 (2000); Wu, et al., *J. Neurosci. Res.*, Vol. 72, pg. 393 (2003)) and cardiac disorders (Tomita, et al., *Circulation*, Vol. 100, pg. 247 (1999). Shake, et al., *Ann. Thorac. Surg.*, Vol. 73, pg. 1919 (2002)). Importantly, promising results also have been reported in clinical trials for osteogenesis imperfecta (Horowitz, et al., *Blood*, Vol. 97, pg. 1227 (2001); Horowitz, et al. *Proc. Nat. Acad. Sci.*, Vol. 99, pg. 8932 (2002)) and enhanced engraftment of heterologous bone marrow transplants (Frassoni, et al., *Int. Society for Cell Therapy*, SA006 (abstract) (2002); Koc, et al., *J. Clin. Oncol.*, Vol. 18, pgs. 307-316 (2000)).

In addition, in vitro studies from different laboratories have shown that MSCs can inhibit T-cell proliferation either in mixed lymphocyte cultures or by other stimuli such as antigens and mitogens (Di Nicola, et al., *Blood*, Vol. 99, pgs. 3638-3843 (2002); Tse, et al., *Transplantation*, Vol. 75, pgs. 389-397 (2003); Aggarwal, et al., *Blood*, Vol. 105, pgs. 1815-1822 (2005)). Recent in vitro data demonstrate further that MSCs decrease the secretion of pro-inflammatory cytokines, tumor necrosis factor-α (TNF-α), and Interferon-γ (IFN-γ), and simultaneously increase production of anti-inflammatory cytokines Interleukin-10 (IL-10) and Interleukin-4 (IL-4) by immune cells. (Aggarwal, 2005). These results indicate that due to immunomodulatory and anti-inflammatory activities, MSCs can be beneficial for treatment of immunological responses which occur in graft-versus-host disease (GVHD), solid organ transplantation, and autoimmune diseases such as multiple sclerosis and rheumatoid arthritis. A clinical case report demonstrating the therapeutic effect of MSCs for acute GVHD supports strongly this hypothesis. (Le Blanc, et al., *The Lancet*, Vol. 363, pgs. 1439-1441 (2004).)

The TNF-α receptors are expressed on the surface of mesenchymal stem cells. Accumulated data indicate that TNF-α is an important regulator of mesenchymal stem cell function. Incubation of TNF-α with human mesenchymal stem cells in culture upregulates prostaglandin E2 ($PGE_2$) and keratinocyte growth factor (KGF) secretion, induces indoleamine 2,3 deoxygenase (IDO) enzyme activity and stimulates cell migration. TNF-α has been shown to be present at wound and inflammatory sites, especially in organs targeted by graft-versus-host disease. (Kolde, et al., *Transplantation*, Vol. 64, pgs. 518-524 (1997), Kuroiwa, et al., *J. Clin. Invest.*, Vol. 107, pgs. 1365-1373 (2001); Deans, et al., *Exp. Hematol.*, Vol. 28, pgs. 875-884 (2002); Ellison, et al., *J. Clin. Immunol.*, Vol. 24, pgs. 197-211 (2004)). Thus, such data indicate that expression of TNF-α receptors by mesenchymal stem cells may be critical for immunosuppressive, immunomodulatory, anti-inflammatory, tissue-repairing, or wound-healing activities, as well as migration to sites of inflammation.

There are two types of TNF-α receptors, or TNFRs: Type I (TNFRI), also known as p55, and Type II (TNFRII), also known as p75. (Tartaglia, et al., *Proc. Nat. Acad. Sci*, Vol. 88, pgs. 9292-9296 (1991).) Both types of TNF-α receptors are present on MSCs; however, TNFRI is the predominant type. (Vancherl, et al., *Am. J. Respir. Cell Mol. Biol.*, Vol. 22, pgs. 628-634 (2000); Debets, et al., *Cytokine*, Vol. 8, pgs. 80-88 (1996).)

The invention now will be described with respect to the drawings wherein.

Figure 1:
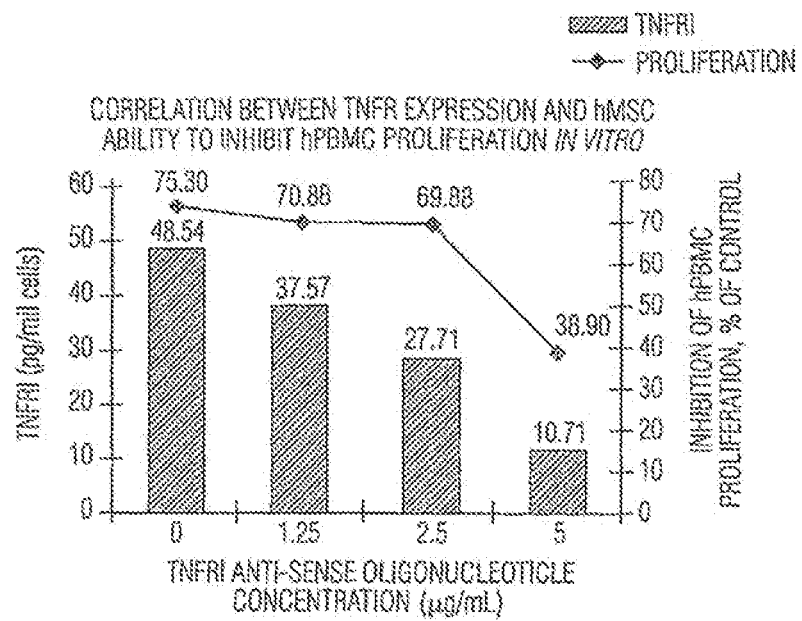
FIG. 1 is a graph of the correlation between TNFRI expression and the ability of MSCs to inhibit PBMC proliferation in vitro.

In accordance with an aspect of the present invention, there is provided a composition comprising mesenchymal stem cells. The mesenchymal stem cells express the TNF-α receptor Type I (TNFRI) in an amount effective to inhibit the proliferation of lymphocytes. In one embodiment, the mesenchymal stem cells express TNFRI in an amount of at least 13 pg/$10^6$ cells. In another embodiment, the mesenchymal stem cells express TNFRI in an amount of at least 15 pg/$10^6$ cells. In yet another embodiment, the mesenchymal stem cells express TNFRI in an amount of at least 18 pg/$10^6$ cells.

Although the scope of the present invention is not to be limited to any theoretical reasoning, Applicants have found that mesenchymal stem cells which express the TNF-α receptor Type I in an amount from at least 13 pg/$10^6$ cells inhibit the proliferation of lymphocytes. Such mesenchymal stem cells are particularly useful in inhibiting immune responses, and more particularly such mesenchymal stem cells are useful in the treatment of graft-versus-host disease; solid organ transplant rejection such as, for example, heart transplant rejection, liver transplant rejection, pancreas transplant rejection, intestine transplant rejection, and kidney transplant rejection; and autoimmune diseases such as, for example, rheumatoid arthritis, multiple sclerosis, Type I diabetes, Crohn's disease, Guillain-Barré syndrome, lupus erythematosus, myasthenia gravis, optic neuritis, psoriasis, Graves' disease, Hashimoto's disease, Ord's thyroiditis, aplastic anemia, Reiter's syndrome, autoimmune hepatitis, primary biliary cirrhosis, antiphospholipid antibody syndrome, opsoclonus myoclonus syndrome, temporal arteritis, acute disseminated encephalomyelitis, Goodpasture's syndrome, Wegener's granulomatosis, coeliac disease, pemphigus, polyarthritis, warm autoimmune hemolytic anemia, and scleroderma.

In one embodiment, the mesenchymal stem cells are obtained from a mammal. The mammal may be a primate, including human and non-human primates.

The mesenchymal stem cells may be a homogeneous composition or may be a mixed cell population enriched in MSCs. Homogeneous mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

The amount of cellular TNF-α receptor, such as TNF-α receptor Type I, that is expressed in a culture of mesenchymal stem cells may be determined by methods known to the skilled in the art. Such methods include, but are not limited to, quantitative assays such as quantitative ELISA assays, for example. It is to be understood, however, that the scope of the present invention is not to be limited to any particular method for determining the amount of TNF-α receptor.

In one embodiment, the amount of TNF-α receptor expressed by a culture of mesenchymal stem cells is determined by an ELISA assay. In such an assay, a cell lysate from a culture of mesenchymal stem cells is added to a well of an ELISA plate. The well may be coated with an antibody, either a monoclonal or a polyclonal antibody(ies), against the TNF-α receptor. The well then is washed, and then contacted with an antibody, either a monoclonal or a polyclonal antibody(ies), against the TNF-α receptor. The antibody is conjugated to an appropriate enzyme, such as horseradish peroxidase, for example. The well then may be incubated, and then is washed after the incubation period. The wells then are contacted with an appropriate substrate, such as one or more chromogens. Chromogens which may be employed include, but are not limited to, hydrogen peroxide and tetramethylbenzidine. After the substrate(s) is (are) added, the well is incubated for an appropriate period of time.

Upon completion of the incubation, a "stop" solution is added to the well in order to stop the reaction of the enzyme with the substrate(s). The optical density (OD) of the sample then is measured. The optical density of the sample is correlated to the optical densities of samples containing known amounts of TNF-α receptor in order to determine the amount of TNF-α receptor expressed by the culture of mesenchymal stem cells being tested.

Thus, the present invention provides for the selection of a population of mesenchymal stem cells which express TNF-α receptor Type I in an amount of at least 13 pg/$10^6$ cells. Such selected mesenchymal stem cells then may be admixed with an appropriate pharmaceutical carrier for treatment of the diseases and disorders mentioned hereinabove. For example, the mesenchymal stem cells may be administered as a cell suspension including a pharmaceutically acceptable liquid medium for injection.

The mesenchymal stem cells of the present invention are administered to an animal in an amount effective to treat one or more of the above-mentioned diseases or disorders in the animal. The animal may be a mammal, and the mammal may be a primate, including human and non-human primates. The mesenchymal stem cells may be administered systemically, such as, for example, by intravenous, intraarterial, or intraperitoneal administration. The exact dosage of mesenchymal stem cells to be administered is dependent upon a variety of factors, including, but not limited to, the age, weight, and sax of the patient, the disease(s) or disorder(s) being treated, and the extent and severity thereof.

The invention now will be described with respect to the following examples; however, the scope of the present invention is not intended to be limited thereby.

EXAMPLE 1

In order to investigate the role of TNFRI on the immunosuppressive hMSC activity, hMSCs were transfected transiently by antisense TNFRI type oligonucleotides with the purpose to decrease TNFRI expression (Shen et al., *J. Biol. Chem.*, Vol. 272, pgs. 3550-3553 (1997)). In order to reach different degrees of TNFRI expression inhibition, three different concentrations of oligonucleotides were used for transfection experiments. Non-transfected MSCs and MSCs transfected with a sense oligonucleotide were used as controls. TNFRI expression on hMSCs was analyzed in cell lysates by ELISA, and effect of reduction in TNFRI expression on hMSC capacity to inhibit hPBMC proliferation in vitro was investigated.

Human bone marrow-derived MSCs at Passage 5 from 7 different donors were used for analysis. Cells were obtained from bone marrow aspirates, and isolated using hespan. The cells then were cultured through Passage 5, and frozen in a standard cryopreservation solution containing 5% human serum albumin (HSA) and 10% dimethylsulfoxide in Plasmalyte A. (Baxter) The cells were stored at −80° C. prior to analysis. On the day of the experiment, the hMSCs were thawed, counted, and plated into 6-well tissue culture plates at $2.5 \times 10^5$ cells/well. After overnight incubation, cells were transfected with TNFRI sense or antisense oligonucleotides at concentrations of 1.25, 2.5 and 5 μg/mL according to the transfection reagent manufacturer's protocol (Invitrogen, the Cellfectin transfection reagent product insert). At 24 hours post-transfection, the cells were collected from the plates. One group of cells was lysed, and expression of TNFRI in cell lysates was analyzed by ELISA according to the sTNFRI ELISA protocol (R&D Systems, product insert). TNFRI expression was expressed in pg of receptor per $1 \times 10^6$ cells.

For the ELISA assay, $2.5 \times 10^5$ MSCs per well were lysed directly in wells using 250 μl/well of Cell Lytic-mammalian cell lysis/extraction reagent (Sigma, Catalog No. C-2978) containing a complete protein inhibitor cocktail (Roche). The cell lysates then were centrifuged for 10 minutes at 12,000-14,000 rpm in an Eppendorf centrifuge to remove insoluble material from the lysis buffer solution. The cell lysates then were collected in an new tube for use in the ELISA assay.

An alternative method of cell lysis, i.e., lysis of cell pellets in tubes, also was carried out for frozen cells and for cells collected from tissue culture plates or flasks. Both methods, direct cell lysis in culture plates and lysis of cell pellets in tubes, gave comparable results.

A commercially available ELISA kit, Quantikine®, Human sTNFRI (Catalog No. DRT 100, R&D Systems) was used for the detection of TNFRI in cell lysates. This assay provides for the measurement of both soluble as well as cell-associated TNFRI (Ojwang, et al., *Biochemistry*, Vol. 36, pg. 6033 (1997).) The assay employs the quantitative sandwich enzyme immunoassay technique. The assay employs a microplate that includes wells that have been pre-coated with a monoclonal antibody specific for TNFRI. TNFRI present in calibrator samples, quality control samples, or samples of MSC cell lysates is captured by the immobilized TNFRI antibody. After washing away any unbound substances, enzyme-linked polyclonal antibodies specific for TNFRI is added to the wells. Following a wash step to remove any unbound enzyme-linked antibody, a substrate solution was added to the wells, and color develops in proportion to the amount of bound TNFRI. The color development then is stopped, and the intensity of the color is measured using an ELISA reader.

The details of the ELISA are given hereinbelow.

50 µl of assay diluent HD1-7, a buffered protein base with preservative, were added to the wells of an ELISA plate. The wells were coated with a monoclonal antibody specific for TNFRI. 200 µl of either calibrator samples (containing 500 pg/ml, 250 pg/ml, 125 pg/ml, 62.5 pg/ml, 31.25 pg/ml, 15.625 pg/ml, or 7.813 pg/ml of soluble human TNFRI), quality control samples (containing 45 pg/ml, 100 pg/ml, or 250 pg/ml of human TNFRI), or cell lysates then were added to the wells. Prior to the addition of the calibration and quality control sample to the wells, such samples were treated with the Cell Lytio-mammalian cell lysis extraction agent (Sigma) and complete protein inhibitor cocktail (Roche) as hereinabove described. The plate than was covered with an adhesive strip, and incubated for 2 hours±10 minutes at room temperature.

The liquid then was decanted from each well by inverting the plate over a sink, and then the plate was washed three times. The plate is washed each time with 400 µl of a wash buffer added to each well. Residual liquid was removed by inverting the plate and blotting.

200 µl of soluble TNFRI polyclonal antibodies conjugated to horseradish peroxidase then were added to each well. The plate then was incubated for 2 hours±10 minutes at room temperature. The liquid then was decanted from each well, and each well was washed three times with 400 µl of wash buffer as hereinabove described.

200 µl of a substrate solution of stabilized hydrogen peroxide and stabilized tetramethylbenzidine chromogen then were added to each well. The plate then was incubated for 20 minutes±10 minutes at room temperature in the dark. 50 µl of a solution of 2N sulfuric acid the were added to each well. The optical density (OD) of each sample then was measured within 30 minutes with a 450 nm test and a 570 nm reference filter. The optical density values then were correlated to the amounts of TNFRI in the cell lysate samples.

Quantitation was achieved by comparing the signal from samples of MSC cell lysates to TNFRI standards assayed at the same time. Each ELISA run provided a calibration curve and included duplicate quality control samples plated in front and after test samples. Quality control samples were used for ELISA run validity assessment. TNFRI expression data were expressed in picograms of receptor per $1 \times 10^6$ cells. The raw data (in pg/ml) reflect TNFRI in picograms per $1 \times 10^6$ cells ($2.5 \times 10^5$ cells were lysed in 250 µl of the lysis reagent, thus corresponding to $1 \times 10^6$ cells/ml).

The ELISA values for the calibration samples are given in Table 1 below.

TABLE 1

| | | | | | | | | |
|---|---|---|---|---|---|---|---|---|
| Calculations for ELISA run calibration standards | | | | | | | | |
| Calibrator Sample | Theoretical Concentration of Calibratiors (pg/mL) | OD* Values | OD Mean Value | Standard Deviation | Back Calculated Concentration for Standards (pg/mL) | Calculated Mean Concentration for Standards (pg/mL) | % DFT* | % CV* |
| St01 | 500 | 2.431 | 2.437 | 0.008 | 498.003 | 499.923 | −0.015 | 0.3 |
|  |  | 2.443 |  |  | 501.842 |  |  |  |
| St02 | 250 | 1.487 | 1.476 | 0.016 | 252.746 | 250.306 | 0.123 | 1.1 |
|  |  | 1.464 |  |  | 247.867 |  |  |  |
| St03 | 125 | 0.804 | 0.815 | 0.015 | 122.64 | 124.447 | −0.442 | 1.8 |
|  |  | 0.825 |  |  | 126.255 |  |  |  |
| St04 | 62.5 | 0.453 | 0.442 | 0.016 | 64.774 | 63.024 | 0.839 | 3.5 |
|  |  | 0.431 |  |  | 61.274 |  |  |  |
| St05 | 31.25 | 0.25 | 0.239 | 0.016 | 32.749 | 30.939 | −0.996 | 6.8 |
|  |  | 0.227 |  |  | 29.128 |  |  |  |
| St06 | 15.625 | 0.143 | 0.145 | 0.002 | 15.765 | 16.007 | 2.446 | 1.5 |
|  |  | 0.146 |  |  | 16.249 |  |  |  |
| St07 | 7.813 | 0.092 | 0.093 | 0.001 | 7.368 | 7.537 | −3.528 | 1.5 |
|  |  | 0.094 |  |  | 7.706 |  |  |  |

*Note: OD—optical density; % DFT—% Difference from Theoretical; CV %—% Coefficient of Variance The ELISA values for the quality control samples are given in Table 2 below.

TABLE 2

Calculations for ELISA run Quality Control (QC) samples

| QC Samples: | Theoretical Concentrations for QCs (pg/mL) | OD* Values | OD Mean Value | Standard Deviation | Back Calculated Concentration for QCs (pg/mL) | Calculated Mean Concentration for QCs (pg/mL) | % DFT* | % CV* |
|---|---|---|---|---|---|---|---|---|
| Front QCs | | | | | | | | |
| QC01 | 45 | 0.366 0.378 | 0.372 | 0.008 | 50.991 52.884 | 51.938 | 15.417 | 2.3 |
| QC02 | 100 | 0.753 0.713 | 0.733 | 0.028 | 113.944 107.2 | 110.572 | 10.572 | 3.9 |
| QC03 | 250 | 1.503 1.515 | 1.509 | 0.008 | 256.165 258.742 | 257.454 | 2.982 | 0.6 |
| Back QCs | | | | | | | | |
| QC01 | 45 | 0.315 0.349 | 0.332 | 0.024 | 42.964 48.312 | 45.638 | 1.418 | 7.2 |
| QC02 | 100 | 0.712 0.683 | 0.698 | 0.021 | 107.033 102.185 | 104.609 | 4.609 | 2.9 |
| QC03 | 250 | 1.547 1.568 | 1.558 | 0.015 | 265.671 270.263 | 267.967 | 7.187 | 1 |

*Note: OD—optical density; % DFT—% Difference from Theoretical; CV %—% Coefficient of Variance Based on the ELISA values for the calibration and quality control samples shown in Tables 1 and 2 hereinabove, TNFRI expression in pg per $1 \times 10^6$ cells for samples of mesenchymal stem cells from the donors were determined. As described hereinabove, the mesenchymal stem cells from each donor were non-transfected, or transfected with a TNFRI sense or antisense oligonucleotide at a concentration of 1.25, 2.5, or 5 µg/ml. The ELISA values and the amount of TNFRI expressed by each of the mesenchymal stem cell samples from each of the donors are given in Table 3 below.

TABLE 3

Calculations for ELISA run test samples

| hMSC Donor # | Sample description: | OD* Values | OD Mean Value | SD* | Calculated Concentration (pg/mL) | Mean Concentration (pg/mL) | TNFRI in pg per $1 \times 10^6$ cells | % CV* |
|---|---|---|---|---|---|---|---|---|
| 24 | Control (non-transfected cells) | 0.385 0.383 | 0.384 | 0.001 | 53.989 53.674 | 53.831 | 53.831 | 0.4 |
| | Control oligo-transfected cells 5 µg/mL | 0.278 0.253 | 0.266 | 0.018 | 37.15 33.211 | 35.186 | 35.186 | 6.7 |
| | Control oligo-transfected cells 2.5 µg/mL | 0.348 0.356 | 0.352 | 0.006 | 48.155 49.415 | 48.785 | 48.785 | 1.6 |
| | Control oligo-transfected cells 1.25 µg/mL | 0.386 0.369 | 0.378 | 0.012 | 54.147 51.464 | 52.806 | 52.806 | 3.2 |
| | TNFRI anti-sense oligo-transfected cells 5 µg/mL | 0.117 0.108 | 0.113 | 0.006 | 11.533 10.047 | 10.79 | 10.79 | 5.7 |
| | TNFRI anti-sense oligo-transfected cells 2.5 µg/mL | 0.254 0.236 | 0.245 | 0.013 | 33.378 30.546 | 31.962 | 31.962 | 5.2 |
| | TNFRI anti-sense oligo-transfected cells 1.25 µg/mL | 0.321 0.3 | 0.311 | 0.015 | 43.907 40.607 | 42.257 | 42.257 | 4.8 |
| 007 | Control (non-transfected cells) | 0.368 0.365 | 0.367 | 0.002 | 51.306 50.833 | 51.07 | 51.07 | 0.6 |
| | Control oligo-transfected cells 5 µg/mL | 0.226 0.212 | 0.219 | 0.01 | 28.97 26.761 | 27.866 | 27.866 | 4.5 |
| | Control oligo-transfected cells 2.5 µg/mL | 0.293 0.25 | 0.272 | 0.03 | 39.507 32.749 | 36.128 | 36.128 | 11.2 |
| | Control oligo-transfected cells 1.25 µg/mL | 0.308 0.263 | 0.286 | 0.032 | 41.864 34.793 | 38.329 | 38.329 | 11.1 |
| | TNFRI anti-sense oligo-transfected cells 5 µg/mL | 0.123 0.104 | 0.114 | 0.013 | 12.517 9.382 | 10.949 | 10.949 | 11.8 |
| | TNFRI anti-sense oligo-transfected cells 2.5 µg/mL | 0.269 0.216 | 0.243 | 0.037 | 35.736 27.393 | 31.565 | 31.565 | 15.5 |

TABLE 3-continued

Calculations for ELISA run test samples

| hMSC Donor # | Sample description: | OD* Values | OD Mean Value | SD* | Calculated Concentration (pg/mL) | Mean Concentration (pg/mL) | TNFRI in pg per $1 \times 10^6$ cells | % CV* |
|---|---|---|---|---|---|---|---|---|
| | TNFRI anti-sense oligo-transfected cells 1.25 µg/mL | 0.313 0.293 | 0.303 | 0.014 | 42.65 39.507 | 41.078 | 41.078 | 4.7 |
| 014 | Control (non-transfected cells) | 0.377 0.383 | 0.38 | 0.004 | 52.726 53.674 | 53.2 | 53.2 | 1.1 |
| | Control oligo-transfected cells 5 µg/mL | 0.251 0.247 | 0.249 | 0.003 | 32.907 32.277 | 32.592 | 32.592 | 1.1 |
| | Control oligo-transfected cells 2.5 µg/mL | 0.338 0.291 | 0.315 | 0.033 | 46.581 39.193 | 42.887 | 42.887 | 10.6 |
| | Control oligo-transfected cells 1.25 µg/mL | 0.356 0.337 | 0.347 | 0.013 | 49.415 46.424 | 47.919 | 47.919 | 3.9 |
| | TNFRI anti-sense oligo-transfected cells 5 µg/mL | 0.11 0.098 | 0.104 | 0.008 | 10.378 8.379 | 9.379 | 9.379 | 8.2 |
| | TNFRI anti-sense oligo-transfected cells 2.5 µg/mL | 0.211 0.2 | 0.206 | 0.008 | 26.603 24.864 | 25.733 | 25.733 | 3.8 |
| | TNFRI anti-sense oligo-transfected cells 1.25 µg/mL | 0.3 0.288 | 0.294 | 0.008 | 40.607 38.722 | 39.664 | 39.664 | 2.9 |
| 015 | Control (non-transfected cells) | 0.475 0.462 | 0.469 | 0.009 | 68.284 66.209 | 67.246 | 67.246 | 2 |
| | Control oligo-transfected cells 5 µg/mL | 0.278 0.28 | 0.279 | 0.001 | 37.15 37.465 | 37.308 | 37.308 | 0.5 |
| | Control oligo-transfected cells 2.5 µg/mL | 0.34 0.345 | 0.343 | 0.004 | 46.896 47.683 | 47.289 | 47.289 | 1 |
| | Control oligo-transfected cells 1.25 µg/mL | 0.419 0.406 | 0.413 | 0.009 | 59.37 57.31 | 58.34 | 58.34 | 2.2 |
| | TNFRI anti-sense oligo-transfected cells 5 µg/mL | 0.13 0.12 | 0.125 | 0.007 | 13.658 12.025 | 12.842 | 12.842 | 5.7 |
| | TNFRI anti-sense oligo-transfected cells 2.5 µg/mL | 0.253 0.27 | 0.262 | 0.012 | 33.221 35.893 | 34.557 | 34.557 | 4.6 |
| | TNFRI anti-sense oligo-transfected cells 1.25 µg/mL | 0.377 0.384 | 0.381 | 0.005 | 52.726 53.831 | 53.279 | 53.279 | 1.3 |
| 23 | Control (non-transfected cells) | 0.260 0.249 | 0.255 | 0.008 | 40.591 38.672 | 39.632 | 39.632 | 3.1 |
| | Control oligo-transfected cells 5 µg/mL | 0.191 0.177 | 0.184 | 0.010 | 28.560 26.117 | 27.339 | 27.339 | 5.4 |
| | Control oligo-transfected cells 2.5 µg/mL | 0.216 0.203 | 0.209 | 0.009 | 32.919 30.653 | 31.786 | 31.786 | 4.4 |
| | Control oligo-transfected cells 1.25 µg/mL | 0.222 0.222 | 0.222 | 0.000 | 33.965 33.965 | 33.965 | 33.965 | 0.0 |
| | TNFRI anti-sense oligo-transfected cells 5 µg/mL | 0.107 0.105 | 0.106 | 0.001 | 13.798 13.441 | 13.620 | 13.620 | 1.3 |
| | TNFRI anti-sense oligo-transfected cells 2.5 µg/mL | 0.206 0.168 | 0.187 | 0.027 | 31.176 24.544 | 27.860 | 27.860 | 14.4 |
| | TNFRI anti-sense oligo-transfected cells 1.25 µg/mL | 0.213 0.211 | 0.212 | 0.001 | 32.396 32.048 | 32.222 | 32.222 | 0.7 |
| 486 | Control (non-transfected cells) | 0.249 0.248 | 0.249 | 0.001 | 41.244 41.053 | 41.148 | 41.148 | 0.3 |
| | Control oligo-transfected cells 5 µg/mL | 0.149 0.123 | 0.136 | 0.018 | 22.401 17.560 | 19.981 | 19.981 | 13.5 |
| | Control oligo-transfected cells 2.5 µg/mL | 0.246 0.215 | 0.231 | 0.022 | 40.672 34.792 | 37.732 | 37.732 | 9.5 |
| | Control oligo-transfected cells 1.25 µg/mL | 0.263 0.242 | 0.253 | 0.015 | 43.915 39.911 | 41.913 | 41.913 | 5.9 |
| | TNFRI anti-sense oligo-transfected cells 5 µg/mL | 0.071 0.065 | 0.068 | 0.004 | 7.917 6.805 | 7.361 | 7.361 | 6.2 |
| | TNFRI anti-sense oligo-transfected cells 2.5 µg/mL | 0.142 0.142 | 0.142 | 0.000 | 21.096 21.096 | 21.096 | 21.096 | 0.0 |
| | TNFRI anti-sense oligo-transfected cells 1.25 µg/mL | 0.193 0.164 | 0.179 | 0.021 | 30.644 25.204 | 27.924 | 27.924 | 11.5 |
| 13 | Control (non-transfected cells) | 0.211 0.207 | 0.209 | 0.003 | 34.037 33.282 | 33.659 | 33.659 | 1.4 |
| | Control oligo-transfected cells 5 µg/mL | 0.134 0.133 | 0.134 | 0.01 | 19.606 19.420 | 19.513 | 19.513 | 0.5 |
| | Control oligo-transfected cells 2.5 µg/mL | 0.195 0.180 | 0.188 | 0.011 | 31.020 28.201 | 29.611 | 29.611 | 5.7 |

TABLE 3-continued

Calculations for ELISA run test samples

| hMSC Donor # | Sample description: | OD* Values | OD Mean Value | SD* | Calculated Concentration (pg/mL) | Mean Concentration (pg/mL) | TNFRI in pg per $1 \times 10^6$ cells | % CV* |
|---|---|---|---|---|---|---|---|---|
| | Control oligo-transfected cells 1.25 µg/mL | 0.207 0.176 | 0.192 | 0.022 | 33.282 27.451 | 30.366 | 38.329 | 11.4 |
| | TNFRI anti-sense oligo-transfected cells 5 µg/mL | 0.087 0.073 | 0.080 | 0.010 | 10.882 8.288 | 9.585 | 9.585 | 12.4 |
| | TNFRI anti-sense oligo-transfected cells 2.5 µg/mL | 0.156 0.113 | 0.135 | 0.030 | 23.708 15.703 | 19.706 | 19.706 | 22.6 |
| | TNFRI anti-sense oligo-transfected cells 1.25 µg/mL | 0.208 0.140 | 0.174 | 0.048 | 33.470 20.723 | 27.097 | 27.097 | 27.6 |

*Note: OD—optical density; SD—Standard Deviation; CV %—% Coefficient of Variance From the above data shown in Table 3, the mean TNFRI expression, in picograms per $1 \times 10^6$ cells, was determined for non-transfected (control) mesenchymal stem cells, as well as mesenchymal stem cells transfected with 1.25, 2.5, or 5 µl/ml of antisense or sense oligonucleotide. The mean TNFRI expression values are given in Table 4 below.

TABLE 4

TNFRI expression by hMSCs transfected with anti-sense and control (sense) oligonucleotides: summary for 7 tested hMSC donors

| | TNFRI expression in pg per $1 \times 10^6$ cells | | | | | | | Mean for | |
|---|---|---|---|---|---|---|---|---|---|
| hMSC donor #: | 486 | 13 | 24 | 007 | 14 | 15 | 23 | 7 donors | SD |
| Control (non-transfected cells) | 41* | 34 | 54 | 51 | 53 | 67 | 40 | 48.57 | 11.09 |
| TNFRI anti-sense oligo-transfected cells 5 µg/mL | 7 | 10 | 11 | 11 | 9 | 13 | 14 | 10.71 | 2.36 |
| TNFRI anti-sense oligo-transfected cells 2.5 µg/mL | 21 | 20 | 32 | 32 | 26 | 35 | 28 | 27.71 | 5.74 |
| TNFRI anti-sense oligo-transfected cells1.25 µg/mL | 28 | 27 | 42 | 41 | 40 | 53 | 32 | 37.57 | 9.22 |
| Control (sense) oligo-transfected cells 5 µg/mL | 20 | 20 | 35 | 28 | 33 | 37 | 27 | 28.57 | 6.85 |
| Control (sense) oligo-transfected cells 2.5 µg/mL | 38 | 30 | 49 | 36 | 43 | 47 | 32 | 39.29 | 7.30 |
| Control (sense) oligo-transfected cells 1.25 µg/mL | 42 | 30 | 53 | 38 | 48 | 58 | 34 | 43.29 | 10.21 |

*Note: These values represent mean TNFRI numbers (from table 3, column 8: "TNFRI in pg per $1 \times 10^6$ cells") rounded to whole numbers A second group of transfected cells was used for investigation of the effect of hMSCs on hPBMC proliferation in vitro. Human PBMCs from two different donors were used for this assay. PBMCs were isolated from leukopheresed blood using Ficoll-Paque gradient centrifugation according to the manufacturer's protocol (Amersham Biosciences, Ficoll-Paque Plus product insert). Cells were stored frozen at −80° C. in a medium including 90% FBS and 10% DMSO prior to analysis. On the day of the experiment hPBMCs were thawed, counted and plated into 96-well tissue culture plates at $1 \times 10^5$ cells/well together with hMSCs ($1 \times 10^4$ cells/well). A combination of anti-CD3 (1 µg/mL) and anti-CD28 (1 µg/mL) antibodies was used to stimulate lymphocyte proliferation that represents an in vitro model for immune cell activation characteristics of GVHD and rejection of allogeneic organs. (Trickett, et al., J. Immunol. Methods, Vol. 275, pgs. 251-255 (2003); Koulova, et al., J. Exp. Med., Vol. 173, No. 3, pgs. 759-762 (1991); Foster, et al., Transplantation, Vol. 76, No. 6; Czitrom, Clin. Ortho. Relat. Res., Vol. 326, pgs. 11-24 (1996)). The plates then were incubated in a humidified atmosphere containing 5% $CO_2$. The proliferation of PBMCs alone and in the presence of MSCs was measured at day 5 from culture initiation by the addition of [Methyl-$^3$H]-thymidine at 1 µCi/well for the final 18-20 hrs of culture. After labeling, the cells were transferred onto a glass filter using a 96-well plate harvester, and radioactivity incorporated into DNA was measured by a liquid scintillation beta-counter. The uptake of [Methyl-$^3$H]-thymidine into DNA in counts per minute (cpm) represents hPBMC proliferation. Final results were expressed as % inhibition of PBMC proliferation in the presence of MSCs calculated as:

100%−[Proliferation(PBMC+MSC, cpm)×100/Proliferation(PBMC, cpm)]

The results for the mesenchymal stem cells from each of the donors are given in Table 5 below.

TABLE 5

Inhibition of CD3/CD28-induced hPBMC proliferation by hMSCs transfected with anti-sense and control (sense) oligonucleotides: summary for 7 tested hMSC donors

| hMSC donor #: | % inhibition of hPBMC proliferation by hMSCs | | | | | | | | | | Mean % for 7 donors | SD |
|---|---|---|---|---|---|---|---|---|---|---|---|---|
| | 486 | | 13 | 24 | 007 | 14 | 15 | | 23 | | | |
| hPBMC donor #: | 2 | 3 | 2 | 3 | 3 | 3 | 3 | 2 | 2 | 3 | | |
| Control (non-transfected cells) | 65 | 73 | 82 | 94 | 70 | 66 | 82 | 62 | 68 | 91 | 75.30 | 11.26 |
| TNFRI anti-sense oligo-transfected cells 5 µg/mL | 40 | 45 | 46 | 68 | 32 | 10 | 39 | 19 | 38 | 52 | 38.90 | 16.29 |
| TNFRI anti-sense oligo-transfected cells 2.5 µg/mL | 83 | 90 | 59 | 86 | ND | 73 | ND | 63 | 47 | 58 | 69.88 | 15.48 |
| TNFRI anti-sense oligo-transfected cells 1.25 µg/mL | 62 | 74 | 86 | ND | 72 | 64 | 57 | ND | 72 | 80 | 70.88 | 9.58 |
| Control (sense) oligo-transfected cells 5 µg/mL | 38 | 87 | 60 | 77 | 58 | 77 | 62 | 44 | 52 | 53 | 60.80 | 15.50 |
| Control (sense) oligo-transfected cells 2.5 µg/mL | 60 | 91 | 67 | ND | ND | 62 | 66 | 57 | 70 | 95 | 71.00 | 14.22 |
| Control (sense) oligo-transfected cells 1.25 µg/mL | 87 | ND | 68 | 71 | 66 | 68 | 36 | ND | 49 | 85 | 70.57 | 12.77 |

Note:
ND—no data

The above data with respect to inhibition of CD3/CD28 induced PBMC proliferation were correlated to the mean TNFRI expression data shown in Table 4 hereinabove. The correlated data with respect to mean TNFRI expression and inhibition of CD3/CD28 induced PBMC proliferation are given in Table 6 below.

TABLE 6

TNFRI expression and effect on hPBMC proliferation in vitro by hMSCs transfected with TNFRI oligonucleotides

| Human MSCs condition | Oligonucleotide concentration (µg/mL) | % Inhibition of hPBMC proliferation (Mean ± SD) | TNFRI expression in pg/1 × 10⁶ MSCs (Mean ± SD) |
|---|---|---|---|
| Untransfected (Control MSCs) | Not applicable | 75.30 ± 11.26 | 48.57 ± 11.09 |
| Antisense oligonucleotide | 1.25 | 70.88 ± 9.58 | 37.57 ± 9.22 |
| | 2.5 | 69.88 ± 15.48 | 27.71 ± 5.74 |
| | 5 | 38.90 ± 16.29 | 10.71 ± 2.36 |
| Sense oligonucleotide (control oligonucleotide) | 1.25 | 70.57 ± 12.77 | 43.29 ± 10.21 |
| | 2.5 | 71.00 ± 14.22 | 39.29 ± 7.30 |
| | 5 | 60.80 ± 15.50 | 28.57 ± 6.85 |

The results from these experiments show that hMSCs with decreased expression of TNFR type I (TNFRI) lose their ability to suppress hPBMC proliferation in vitro. The data support the premise that the expression of TNFRI is an essential link to the suppression of PBMC proliferation by MSCs. Thus, TNFRI can be used as a potency marker for MSC immunomodulative activity. Based on the obtained data, a potency threshold of 13.07 pg of TNFRI (mean±SD) per 1×10⁶ cells correlates with less than 50% inhibition of hPBMC proliferation (Table 6, FIG. 1). Thus, non-potent MSCs are cells expressing less than 13 pg TNFRI per 1×10⁶ cells.

EXAMPLE 2

TNFRI is a Temperature-sensitive Marker of MSC Functionality

Ex vivo handling of mammalian cells is restricted by a number of factors including temperature. For example, low temperatures such as −80±5° C., or lower, even as low as −135° C. or below (liquid nitrogen) are required for cell storage whereas ex vivo cell expansion requires a temperature of 37±0.5° C. Cell exposure to temperatures outside of the optimal ranges may lead to a decrease in cell functionality or cell death. Mammalian cells are able to withstand short-term minor temperature fluctuations; however, each type of cells has its own temperature tolerance range for cell culture maintenance, shipping, and storage.

The expression level of TNFRI on hMSCs correlates with hMSC immunosuppressive activity. The level of TNFRI expression by hMSCs of less than 13 pg/10⁶ cells has been determined as a threshold, below which hMSCs begin to lose their ability to suppress an immune response (See FIG. 1). Thus, TNFRI expression is a marker of hMSC immunosuppression, an activity that is believed essential for MSCs to be efficacious for treatment of immunological reactions taking place in GVHD, organ rejection, autoimmune diseases, and other diseases. Here, effects of temperature fluctuations during storage of frozen hMSCs as well as the effect of time of exposure of cells to room temperature on expression of TNFRI on hMSCs was investigated.

Figure 2:
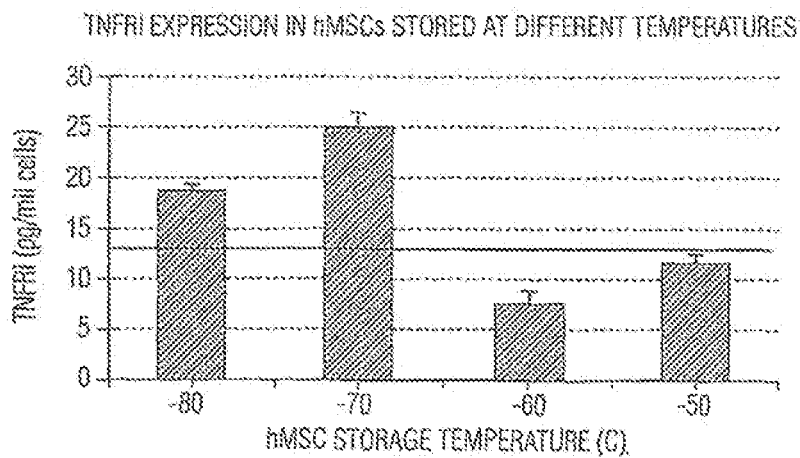
FIG. 2 is a graph showing TNFRI expression by human mesenchymal stem cells stored at −80° C., −70° C., −60° C., and −50° C.

Effect of Store Temperature Fluctuations on TNFRI Expression and hMSC Immunosuppressive Potential The objective of these experiments was to investigate the ability of hMSCs to retain their functional characteristics after an exposure to temperatures above −80° C., which are not optimal temperatures for storage of frozen cells. Human MSCs were frozen at passage 5 and placed for storage in a freezer at −80±5° C. After several weeks, bags of frozen cells were removed from the −80±5° C. freezer and placed at either −70±5° C., −60±5° C., or −50±5° C. for 72±2 hours. After 72±2 hours, the bags were returned to storage at −80±5° C. for at least 24 hours before thaw and analysis. A set of bags moved from one −80±5° C. freezer to another, following the same schedule as the other bags, served as a control. On the day of the experiment the bags containing the cells were thawed, cells were counted, and cell lysates for the TNFRI ELISA were prepared as described in Example 1. The TNFRI ELISA was performed as described in Example 1. Results are summarized in FIG. 2 (bars show mean TNFRI values ±SD for 3 hMSC bags). The data showed that exposure of hMSCs to temperatures of −60±5° C. or −50±5° C. decreases the TNFRI expression level; the level of TNFRI detected by ELISA was below the determined hMSC potency threshold of 13 pg/$10^6$ cells (represented by the solid line on the graph).

Figure 3:
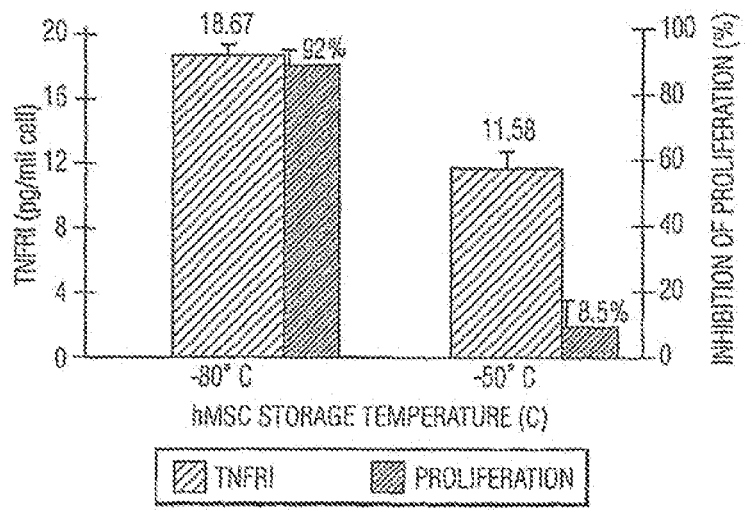
FIG. 3 is a graph showing TNFRI expression and the ability to inhibit PBMC proliferation in vitro, of human mesenchymal stem cells stored at −80° C. and −50° C.

Parallel with TNFRI measurement, two bags with hMSCs stored at −80±5° C. (optimal storage temperature served as a control) and at −50±5° C. (corresponding to a +30° C. greater than the −80±5° C. optimal storage temperature) were used for investigation of hMSC immunosuppressive activity. The ability of the MSCs to suppress anti-CD3/CD28-induced proliferation of hPBMCs in vitro was evaluated as described in Example 1. The results showed that hMSCs stored at −50±5° C. lost their ability to suppress hPBMC proliferation, whereas cells stored at −80±5° c. inhibited hPBMC proliferation by 92% (FIG. 3, dark bars represent mean±SD % inhibition of hPBMC proliferation. Numbers inside the dark bars show numerical values). The immunosuppressive activity of MSCs is dependent on the level of TNFRI expression: cells expressing more than 13 pg/$10^6$ cells of TNFRI, which was determined as an MSC immunosuppressive potential threshold, are biologically active, and cells with the TNFRI level below 13 pg/$10^6$ cells are not (FIG. 3, light bars represent mean±SD of the TNFRI expression level. Numbers inside the light bars show numerical values). Thus, non-optimal storage temperatures decrease TNFRI expression on hMSCs, and which correlates with decrease in hMSC functionality.

Figure 4:
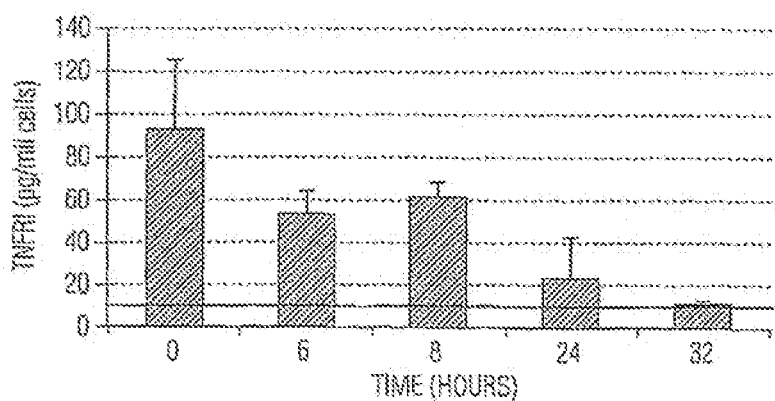
FIG. 4 is a graph showing TNFRI expression by human mesenchymal stem cells stored at −135° C. or below, and then thawed and kept at room temperature for 6, 8, 24, or 32 hours.

Effect of Cell Exposure Time to Room Temperature on TNFRI Expression on hMSC The results of this experiment serve as additional evidence that TNFRI expression on hMSCs is decreasing under cell exposure to non-optimal temperatures. In this experiment the effect of cell suspension storage at room temperature on TNFRI expression was studied. Two hMSC kits were used in the experiment. Bags containing hMSCs were stored at ≦−135° C. prior to the experiment. On the day of the experiment the cells were thawed and diluted with Plasmalyte A physiological solution (Baxter) in a manner that mimics the current cell processing for intravenous hMSC administration at clinical sites. The thawed and diluted hMSCs were kept at room temperature (22° C.-24° C. ), and samples were taken and tested for the amount of TNFRI at 0 (immediately post-thaw—baseline), 6, 8, 10, 24, and 32 hours post-thawing. The results showed that exposure of hMSCs to room temperature decreased the TNFRI expression level on the hMSCs (FIG. 4, bars represent mean±SD of the TNFRI expression level for 2 hMSC lots. The solid line represents the TNFRI expression level of 13 pg/$10^6$ cells, which is the hMSC potency threshold). The significant decrease in TNFRI expression was observed at 24 hours and 32 hours, and it correlated with a significant decrease in cell viability (below 20%, data not shown).

Thus, the experiments described above show that TNFRI expression by hMSCs is sensitive to temperature, and TNFRI can be used as a marker of functionality of hMSC that were exposed to non-optimal temperatures during storage, shipping or cell processing.

The disclosures of all patents, publications, including published patent applications, depository accession numbers, and database accession numbers are hereby incorporated by reference to the same extent as if each patent, publication, depository accession number, and database accession number were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. A method of obtaining mesenchymal stem cells which express TNF-α receptor Type I in an amount of at least 13 pg/$10^6$ cells, comprising:
    obtaining at least one cell population including mesenchymal stem cells from at least one donor;
    determining the amount of TNF-α receptor Type I expressed by the mesenchymal stem cells in each of said at least one cell population; and
    selecting mesenchymal stem cells which express TNF-α receptor Type I in an amount of at least 13 pg/$10^6$ cells;
    wherein said selected mesenchymal stem cells are non-transfected cells.

2. The method of claim 1 wherein said selected mesenchymal stem cells express TNF-α receptor Type I in an amount of at least 15 pg/$10^6$ cells.

3. The method of claim 2 wherein said selected mesenchymal stem cells express TNF-α receptor Type I in an amount of at least 18 pg/$10^6$ cells.

4. The method of claim 1 wherein said mesenchymal stem cells are human mesenchymal stem cells.

5. The method of claim 1 wherein said mesenchymal stem cells are from a single donor.

* * * * *